(12) United States Patent
Brunner et al.

(10) Patent No.: US 7,806,588 B2
(45) Date of Patent: Oct. 5, 2010

(54) METHOD AND SYSTEM FOR ACQUIRING PROJECTION FOR 3D RECONSTRUCTION OF AN OFF-CENTER ROI

(75) Inventors: Thomas Brunner, Nuremberg (DE); Holger Kunze, Bubenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/367,800

(22) Filed: Feb. 9, 2009

(65) Prior Publication Data
US 2009/0202046 A1    Aug. 13, 2009

(30) Foreign Application Priority Data
Feb. 12, 2008    (DE)    ........................ 10 2008 008 750

(51) Int. Cl.
*H05G 1/02*    (2006.01)
(52) U.S. Cl. ........................................ 378/196; 378/62
(58) Field of Classification Search .................... 378/20, 378/62, 193–198
See application file for complete search history.

(56) References Cited

U.S. PATENT DOCUMENTS

| 2005/0203373 | A1 | 9/2005 | Boese et al. | .............. 600/407 |
| 2008/0089467 | A1* | 4/2008 | Lauritsch et al. | .............. 378/20 |

FOREIGN PATENT DOCUMENTS

| DE | 36 04 955 C2 | 3/1994 |
| DE | 20 2005 021 106 U1 | 4/2007 |

* cited by examiner

*Primary Examiner*—Courtney Thomas
(74) *Attorney, Agent, or Firm*—Schiff Hardin LLP

(57) ABSTRACT

In the acquisition of an image series with an x-ray image acquisition that has an x-ray C-arm rotatable around a center point, movement of the patient table is updated so that table is brought into a specific position calculated relative to the angle position of the x-ray C-arm. This position of the patient table is determined as follows. An envelope is established and a point is established that is the center point of a region of interest. In each position of the patient table that matches the position of the x-ray C-arm, the flat panel detector is perpendicular to a line emanating from the point and simultaneously contacts (is tangent to) the envelope. The region of interest is thereby optimally imaged in the image series so that a good 3D reconstruction can be obtained.

4 Claims, 3 Drawing Sheets

METHOD AND SYSTEM FOR ACQUIRING PROJECTION FOR 3D RECONSTRUCTION OF AN OFF-CENTER ROI

BACKGROUND OF THE INVENTION

1. Field of the Invention

The present invention concerns a method to generate an image series for a 3D reconstruction using an x-ray image acquisition system that has an x-ray C-arm rotatable around a center point, the x-ray C-arm carrying an x-ray source and a flat panel detector, and which system has a movable patient table.

2. Description of the Prior Art and Related Subject Matter

A method of the above type is described in DE 10 2006 037 565.3, which was published after the application date of the present application.

A 3D reconstruction of an imaged region of a subject (in particular of a patient) can be derived when images are acquired from different directions. The 3D reconstruction in turn enables the calculation of slice images. In order to acquire the subject from different directions, an x-ray C-arm is conventionally moved in uniform angle intervals over an angle of 180°. An x-ray image (known as a projection) is acquired at each position defined by the angle intervals.

So that a region of interest of the subject can actually be reconstructed, it is necessary for the region to be completely imaged in each of the x-ray images. This is problematical when the region of interest is located beyond the center point of the subject (which typically forms the rotation center). For example, this is the case when the liver of a patient should be imaged. The region of interest that lies outside of the center point of the patient cannot define a new center point for a circular movement because otherwise the x-ray source or the x-ray detector would hit the patient.

In DE 10 2006 037 565.3 it is described to update a subject positioning device (thus a patient table) without collision in the horizontal direction so that a subject region of interest lies within a beam cone of an x-ray beam of the image acquisition system in each rotation angle of the x-ray C-arm in which an image acquisition ensues.

DE 10 2004 004 603 A1 discloses a simulation of a patient table in three dimensions for the purpose of compensation of movements of the patient on the patient table.

DE 10 2006 037 565.3 provides no details of how an updating of the patient table can ensue in multiple dimensions.

SUMMARY OF THE INVENTION

It is an object of the present invention to provide an improvement over the method from DE 10 2006 037 565.3, and to provide details as to how a patient table can be moved so that an optimal 3D reconstruction can be obtained.

The object is achieved by according to the invention wherein an x-ray acquisition system also receives an input that establishes a (closed) envelope in coordinates defined relative to the patient table (and moving with the traveling patient table), and the x-ray image acquisition system also receives an input that establishes a point in a region of interest (inside the envelope).

At each of a number of positions of the x-ray C-arm, an (associated) position of the patient table is calculated such that—given adoption of this position by the patient table coordinated (thus simultaneously at a specific point in time) with the associated position of the x-ray C-arm—the flat panel detector is perpendicular to a straight line emanating from the point in the region of interest and tangentially contacts the envelope.

At each position of the x-ray C-arm the patient table is moved into its associated position calculated as described immediately above, and an x-ray image is (preferably automatically) acquired.

The method according to the invention is a reverse of the method described in DE 10 2006 037 565.3, in which the relative position of patient table and flat panel detector in the manner described above is achieved not by a movement of the patient table but rather solely by a movement of the x-ray C-arm, wherein the x-ray C-arm must be arranged on an articulated arm robot that enables a more complicated movement of the x-ray C-arm. In the inventive method and system, it is sufficient for the x-ray C-arm to be rotated in a known manner around a center point such that x-ray source and flat panel detector move on a circular track, and only the patient table must be suitably moved.

Such an envelope that, given the typical position of the patient on the patient table, surrounds the patient in every case, entered as an input in a suitable manner. The envelope can be formed by two half-ellipses whose parameters are numerically entered, or that are interactively drawn on a monitor by the inputting person. The envelope establishes a limit as to where the patient table can move relative to the flat panel detector. If the envelope surrounds the patient, the fact that the flat panel detector tangentially contacts the envelope means that the flat panel detector does not directly contact the patient. The goal of avoiding a collision of the flat panel detector with the patient is thereby achieved.

As used herein, "tangential contacting of the envelope by the flat panel detector" means that the graphically-represented flat panel detector tangentially contacts the envelope, because the real flat panel detector cannot do so.

Naturally, it is difficult to establish the point in the region of interest without reference to any x-ray images. Therefore, in a preferred embodiment this is done by the x-ray image acquisition system receiving an input that establishes an image acquisition position of the x-ray C-arm and acquires an x-ray image in this image acquisition position at least once (preferably twice) in response to the input. The x-ray image acquisition system additionally subsequently receives an input that establishes a point in the acquired x-ray image or the acquired x-ray images. The region of interest can be recognized particularly well by a physician and an individual point can be established with good definition, in particular when the x-ray C-arm is brought into positions that are perpendicular to one another, in which x-ray images are respectively acquired.

The x-ray image acquisition system according to the invention has a C-arm rotatable around a center point that carries an x-ray source and a flat panel detector; and comprises a patient table that preferably can be moved along two axes perpendicular to the rotation axis of the x-ray C-arm; and a control unit. The control unit is configured to receive a first input and, based on this first input, establish an envelope in coordinates defined relative to the patient table, and to receive a second input and, based on this second input, establish a point in coordinates defined relative to the patient table. The control unit is also configured to calculate an associated position of the patient table at each of a number of positions of the C-arm such that the flat panel detector is perpendicular to a straight line emanating from the point and tangentially contacts the envelope.

The control unit is configured to control position elements for the x-ray C-arm and the patient table so that the C-arm pivots successively through the aforementioned C-arm positions, and the patient table is respectively moved into its associated positions in order to respectively acquire the x-ray images at simultaneous adoption of the associated positions by the C-arm and the patient table.

The x-ray image acquisition system according to the invention can be designed to acquire an x-ray image in response to the receipt of a corresponding input. At least one x-ray image is preferably automatically acquired for each position combination of the x-ray C-arm and patient table, with the control unit correspondingly controlling the x-ray source and the flat panel detector.

DESCRIPTION OF THE PREFERRED EMBODIMENTS

Figure 1:
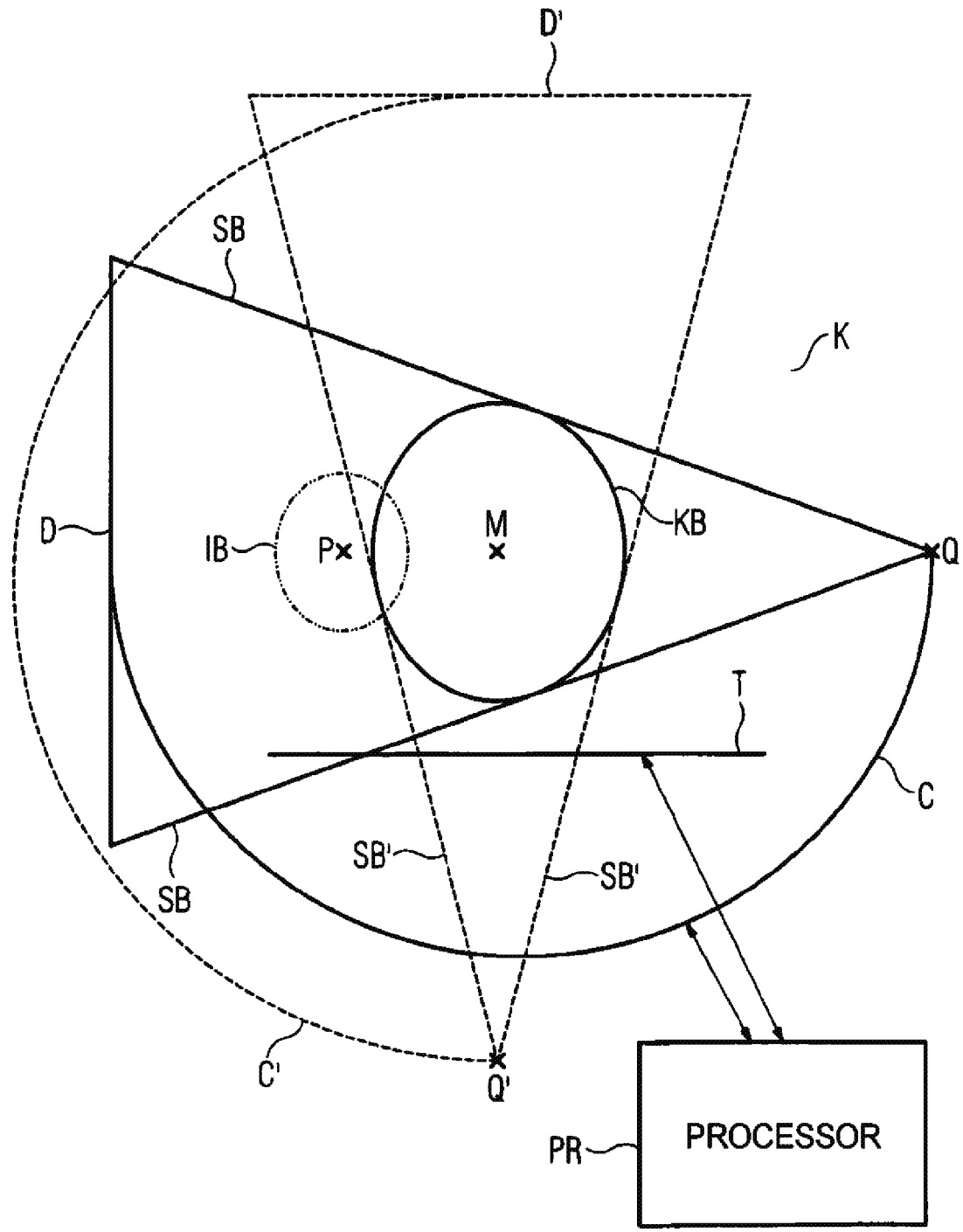
FIG. 1 schematically illustrates the problem underlying the invention, given the acquisition of an image series in the prior art.

A body K is symbolically shown in FIG. 1. Images of the body K are to be acquired with the use of an x-ray image acquisition system. FIG. 1 symbolically illustrates an x-ray source Q and an x-ray detector D. A beam SB emanates from the x-ray source Q and proceeds to the detector D. The x-ray source Q and the detector D are mounted on a C-arm C. The C-arm C is rotated around the center point M of the body K on a table T controlled by a processor PR so that the source Q reaches the position Q' and the detector D reaches the position D'. The beam SB' then passes through the body K. Portions of the body K can be reconstructed based on x-ray images (projections) acquired in the respective angle positions. A three-dimensional reconstruction from a number of such x-ray images that are respectively acquired during rotation of the source Q of the detector D is possible only for the region that is imaged in all (contained) x-ray images. This is the region represented by the circle KB in FIG. 1. A region of interest IB is shown that lies beyond the center point M, and this barely intersects with the circular region KB. The region of interest IB therefore cannot be shown by the 3D reconstruction.

Instead of rotating the x-ray C-arm C around the center point M of the body K, it is theoretically possible to determine the center point P of the region of interest IB and to rotate around this center pin. If the x-ray C-arm C were rotated so that it rotates precisely on a circular path around the center point P of the region of interest IB, the detector D would collide with the body K.

For an optimally good reconstruction of the region of interest IB, it is desirable to achieve a relative movement between the body K and the x-ray source Q and the x-ray detector D so that a rotation around the point P is approximately achieved. This is achieved as follows, in accordance with the invention. An envelope H1, H2 (see FIG. 2) is defined that surrounds the body K in every case and is, in this embodiment elliptical. In a more complicated version, the envelope H1, H2 can be formed as two half-ellipses, wherein one surrounds the back of the patient and the other the chest. In the definition of the envelope H1, H2, orientation is based on the support of the patient on the patient table of the x-ray image acquisition system. It is to be noted that the envelopes H1 and H2 in FIG. 2 in fact appear be barely different from the patient contour K from FIG. 1. The patient contour K, however, is a symbolic drawing whereas the envelopes H1 and H2 can actually have the shape shown in FIG. 2. The shape of the envelope can be programmed in the x-ray image acquisition system (i.e. be input upon starting the operating system), or an input of the envelope H1 or H2 can interactively ensue by a user so that said user can react to individual properties of the patient. For example, the envelope can be made to be smaller if the patient is thinner, and can be made to be larger if the patient is obese.

The region of interest IB is now established by its center points P1, P2 respectively on two x-ray images acquired in advance, between which x-ray source Q and x-ray detector D are respectively moved by 85° to 95° (preferably by 90°). The region of interest is at 01 in one image and is at 02 in the other image. The treating physician can interactively mark a point in both x-ray images using an input device (for example a computer mouse). These points define lines, and the x-ray image acquisition system can then calculate the intersect point of these lines; this intersect point then corresponds to point P.

Figure 2:
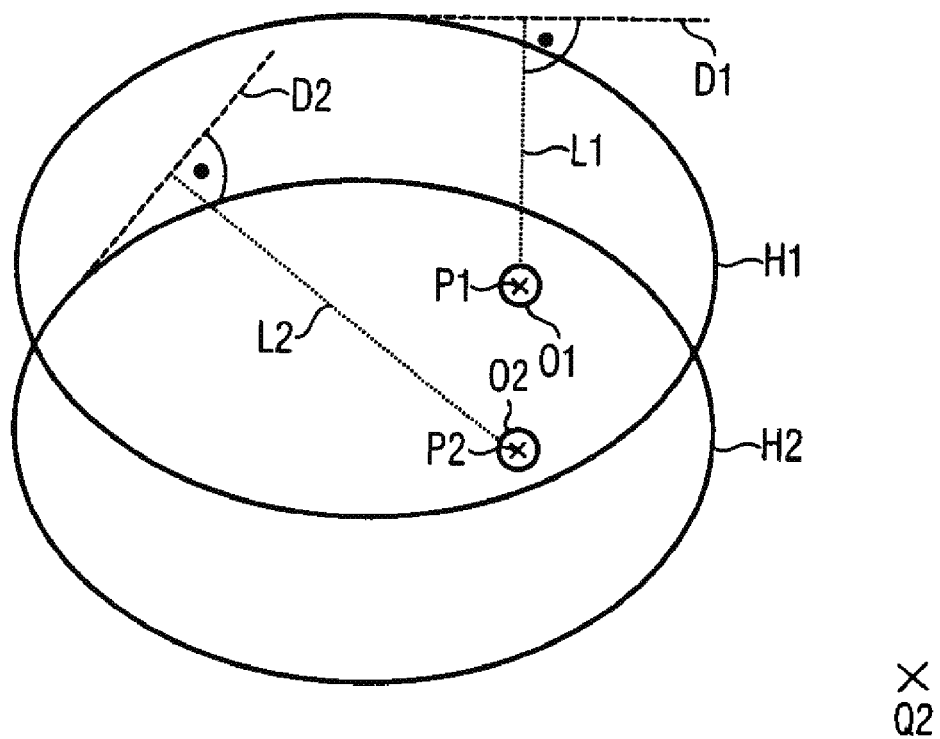
FIG. 2 illustrates the solution, following FIG. 1, for overcoming the problem in accordance with the invention.

While the C-arm C is rotated around the center point M as shown in FIG. 2, the patient must be moved to avoid collisions. This occurs by movement of the patient table T shown in FIG. 1. An associated position of the patient table is calculated for every angle position of the C-arm, thus for every position of x-ray source Q and the detector D, a plane is defined in which the surface of the detector lies for that position of the detector. Straight lines L1, L2 are now drawn in the coordinate system of the x-ray image acquisition system starting from the points P1 and P2, respectively. The straight lines L1, L2, respectively strike the planes D1, D2 of the detector D at a right angle. The envelope H1, H2 that is defined in the coordinate system of the patient table is now moved together with the patient table in the coordinate system of the x-ray image acquisition system, and so that the plane of the detector D1, D2 always is tangent to envelope H1, H2. The position so obtained then defines the associated target position of the patient table that matches the detector position. FIG. 2 shows that, given positioning of the x-ray source Q at the point Q1, the position of the detector corresponding to the dashed line D1 will precisely tangentially contact the envelope as envelope H1 from the dashed line D1 (symbolizing the detector D). A patient table position can be precisely determined in which the envelope is displaced as envelope H2 in comparison to the envelope H1 (naturally with an unchanged basic shape). Given positioning of the x-ray source at point Q2 and the course of the detector D corresponding to the dashed line D2, the envelope H2 then precisely tangentially advances up to the detector D2.

Figure 3:
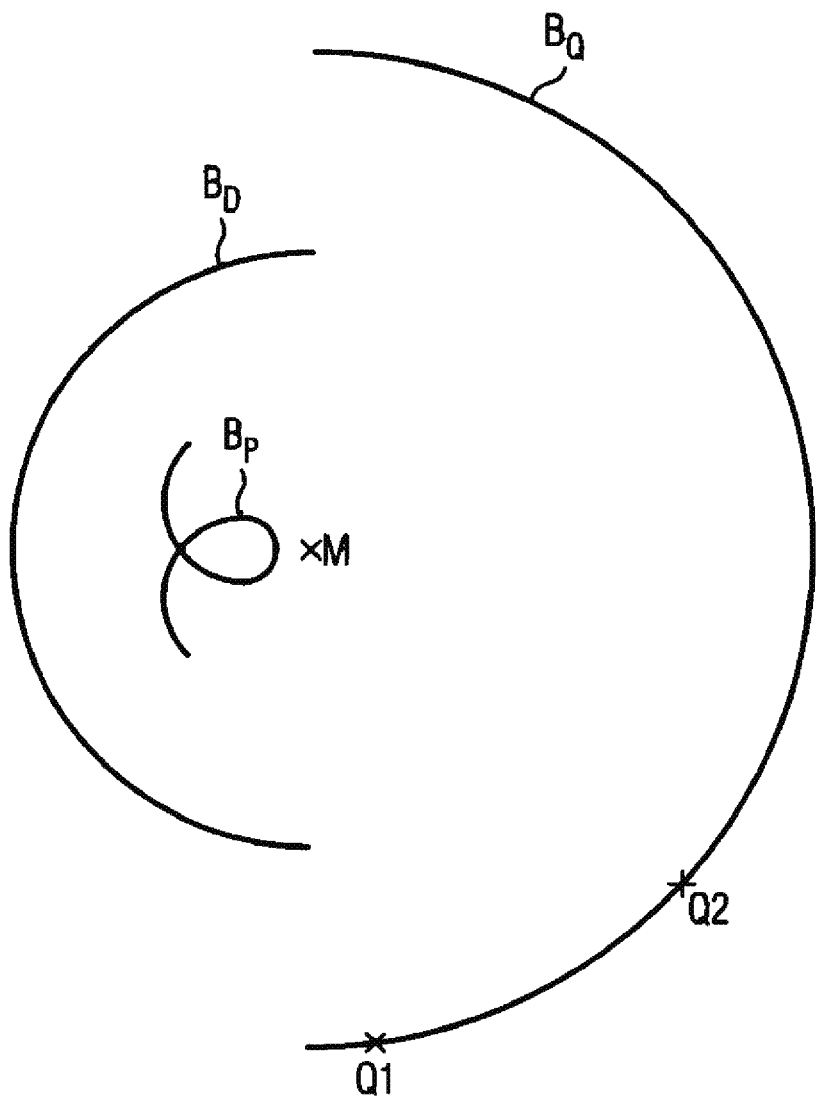
FIG. 3 illustrates the curves traveled by x-ray source, flat panel detector and patient table in the method according to the invention.

FIG. 3 illustrates the paths traversed in the x-ray image acquisition system as a whole, namely the path BQ that the x-ray source travels, the points Q1 and Q2 on the path Q2 (analogous to FIG. 2), and the path BD that traverses a point on the detector. The paths BQ and BD are semi-circles with the same center point M. The path BP traverses a point on the patient table. While the movement of the detector is naturally coupled to that of the x-ray source, the movement of the patient table is a priori independent. However, the movements of the x-ray C-arm C and those of the patient table T can be realized with a certain synchronization. A perfect synchronization is not absolutely necessary.

In the present invention only the acquisition of the image series for 3D reconstruction is of interest, not the 3D reconstruction itself. Methods for such 3D reconstructions based on projections, in which the relative position between x-ray C-arm and patient changes, are known, such as from DE 10 2006 037 564.5. For the 3D reconstruction it is insignificant whether the x-ray C-arm C produces a non-circular path of the x-ray source and the detector, or whether a relative movement is obtained by movement of the patient table T, as in the present method and system.

The method according to the invention enables an optimal imaging of the region of interest IB in the image series so that the 3D reconstruction enables in a particularly good manner the presentation of slice images through the region of interest.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating an image series for 3D reconstruction of an image of a subject using an x-ray imaging system comprising a C-arm, rotatable around a rotational axis, that has an x-ray source and a flat panel x-ray detector mounted thereon, and a patient table movable between the x-ray source and the flat panel x-ray detector, said method comprising the steps of:

in a processor, receiving an input that establishes an envelope in coordinates defined relative to the patient table;

in said processor, receiving an input that establishes a point in a region of interest of the subject;

for each of a plurality of positions of said C-arm around said rotational axis, calculating, in said processor, a position of the patient table, for obtaining image data from said region of interest in the patient on the patient table, for which a radiation-receiving surface of the flat panel detector is perpendicular to a straight line proceeding from said point and for which the radiation receiving surface of the flat panel x-ray detector tangentially contacts said envelope; and moving said C-arm through said plurality of positions and, at each of said positions of the C-arm, moving the patient table into the calculated position associated therewith, and operating said x-ray source and said radiation detector at each position to generate projection data, and making the projection data, acquired from each of said plurality of positions of said C-arm, available as an output from the flat panel x-ray detector for 3D reconstruction of an image of the region of interest.

2. A method as claimed in claim 1 wherein the step of receiving an input that establishes a point in the region of interest comprises:

providing said processor with an input that establishes an image acquisition position of the C-arm;

acquiring at least one x-ray image of the region of interest with the C-arm in said image acquisition position; and from said x-ray image acquired with the C-arm at said image acquisition position, deriving a further input to said processor that establishes a point in the acquired x-ray image that establishes said point in said region of interest.

3. A method as claimed in claim 2 comprising deriving said further input by displaying said x-ray image acquired with said C-arm at said image acquisition position and allowing manual interaction at said display by a user to establish said point in the displayed x-ray image.

4. An imaging system for generating an image series for 3D reconstruction of an image of a subject comprising:

a C-arm, rotatable around a rotational axis, and an x-ray source and a flat panel x-ray detector mounted on said C-arm;

a patient table movable between the x-ray source and the flat panel x-ray detector;

a processor configured to receive an input that establishes an envelope in coordinates defined relative to the patient table and to receive an input that establishes a point in a region of interest of the subject;

said processor being configured to calculate, for each of a plurality of positions of said C-arm around said rotational axis, calculating, a position of the patient table, to obtain image data from said region of interest in the patient on the patient table, for which a radiation-receiving surface of the flat panel detector is perpendicular to a straight line proceeding from said point and for which the radiation receiving surface of the flat panel x-ray detector tangentially contacts said envelope;

said processor being configured to control movement of said C-arm and said patient table to move said C-arm through said plurality of positions and, at each of said positions of the C-arm, to move the patient table into the calculated position associated therewith, and to operate said x-ray source and said radiation detector at each position to generate projection data; and said flat panel x-ray detector making the projection data, acquired from each of said plurality of positions of said C-arm, available as an output from the flat panel x-ray detector in a form for 3D reconstruction of an image of the region of interest therefrom.

* * * * *